United States Patent
Gee, Jr. et al.

(10) Patent No.: US 7,158,660 B2
(45) Date of Patent: Jan. 2, 2007

(54) METHOD AND APPARATUS FOR DETECTING STRUCTURES OF INTEREST

(76) Inventors: James W. Gee, Jr., N2454 Forest Rest La., Lake Geneva, WI (US) 53147; Carl Pennypacker, 231 San Carlos, El Cerrito, CA (US) 94530

( * ) Notice: Subject to any disclaimer, the term of this patent is extended or adjusted under 35 U.S.C. 154(b) by 616 days.

(21) Appl. No.: 10/140,971

(22) Filed: May 8, 2002

(65) Prior Publication Data

US 2003/0210810 A1 Nov. 13, 2003

(51) Int. Cl.
*G06D 9/00* (2006.01)
(52) U.S. Cl. ............... 382/128; 382/130; 382/262; 600/101
(58) Field of Classification Search ........ 382/128–134, 382/262, 254; 600/101; 362/572, 804; 385/117; 606/4; 607/93
See application file for complete search history.

(56) References Cited

U.S. PATENT DOCUMENTS

| | | | |
|---|---|---|---|
| 4,817,622 A | 4/1989 | Pennypacker et al. | |
| 4,995,398 A | 2/1991 | Turnidge | |
| 5,241,170 A | 8/1993 | Field, Jr. et al. | |
| 5,267,331 A | 11/1993 | Siwoff | |
| 5,311,018 A | 5/1994 | Zana et al. | |
| 5,417,688 A | 5/1995 | Elstrom et al. | |
| 5,467,404 A * | 11/1995 | Vuylsteke et al. | 382/274 |
| 5,519,208 A | 5/1996 | Esparza et al. | |
| 5,608,210 A | 3/1997 | Esparza et al. | |
| 5,699,797 A | 12/1997 | Godik | |
| 5,730,133 A | 3/1998 | Godik | |
| 5,747,789 A | 5/1998 | Godik | |
| 5,769,784 A | 6/1998 | Barnett et al. | |
| 5,788,639 A | 8/1998 | Zavislan et al. | |
| 5,865,167 A | 2/1999 | Godik | |
| 5,865,743 A | 2/1999 | Godik | |
| 5,865,829 A | 2/1999 | Katajima | |
| 5,903,660 A * | 5/1999 | Huang et al. | 382/132 |
| 5,910,816 A | 6/1999 | Fontenot | |
| 5,947,906 A | 9/1999 | Dawson, Jr. et al. | |
| 5,997,472 A | 12/1999 | Bonnell et al. | |
| 6,002,958 A | 12/1999 | Godik | |
| 6,010,455 A | 1/2000 | Barnett et al. | |
| 6,032,070 A | 2/2000 | Flock et al. | |
| 6,086,453 A * | 7/2000 | Fukuoka et al. | 451/5 |

(Continued)

OTHER PUBLICATIONS

Jean et al; "Eye Tracking for Image Stabilization"; Lasers in Ophthalmology; 1987, vol. 1, No. 4; pp. 197-204.*

(Continued)

*Primary Examiner*—Jingge Wu
*Assistant Examiner*—Shefali Patel
(74) *Attorney, Agent, or Firm*—Owen J. Bates

(57) ABSTRACT

A method to detect a structure of interest includes shading a target from ambient light. A first plurality of images is acquired from the target. Background in the first plurality of images is reduced to minimize or eliminate brightness variation in the images and to generate a first plurality background-reduced images. A second plurality of images is acquired from the target. Background in the second plurality of images is reduced to generate a second plurality of background-reduced images. Noise in the second plurality of background-reduced images is reduced to generate a noise-reduced image, which is then multiplied to generate an amplified image. A structure of interest is detected in the amplified image. An imaging device that can be used to carry out the method is also included and includes an illuminator that shades the target from ambient light and scatters light.

13 Claims, 8 Drawing Sheets

U.S. PATENT DOCUMENTS

| | | |
|---|---|---|
| 6,178,340 B1 | 1/2001 | Svetliza |
| 6,192,262 B1 | 2/2001 | Godik |
| 6,230,046 B1 | 5/2001 | Crane et al. |
| 6,248,066 B1 | 6/2001 | Barnett et al. |
| 6,263,233 B1 | 7/2001 | Zavislan et al. |
| 6,270,464 B1 | 8/2001 | Fulton, III et al. |
| 6,405,072 B1 * | 6/2002 | Cosman .................. 600/426 |
| 6,411,729 B1 * | 6/2002 | Grunkin .................. 382/132 |
| 6,690,965 B1 * | 2/2004 | Riaziat et al. ............. 600/428 |
| 6,766,042 B1 * | 7/2004 | Freeman et al. ........... 382/128 |
| 6,771,325 B1 * | 8/2004 | Dewald et al. ............ 348/743 |
| 6,834,238 B1 * | 12/2004 | Hochman .................. 702/21 |

OTHER PUBLICATIONS

A to Z of Image Processing Concepts, http://www.dai.ed.ac.uk/HIPR2/glossary.htm, p. 1 (Jan. 10, 2002).

Spatial Filters—Median Filter, http://www.dai.ed.ac.uk/HIPR2/median.htm, pp. 1-6, (Jan. 10, 2002).

Glossary—Pixels, http://www.dai.ed.ac.uk/HIPR2/pixel.htm. p. 1.

Image Arithmetic—Pixel Addition, http://www.dai.ed.ac.uk/HIPR2/pixadd.htm, pp. 1-6 (Jan. 10, 2002).

Image Synthesis—Noise Generation, http://www.dai.ed.ac.uk/HIPR2/noise.htm, pp. 1-6 (Jan. 10, 2002).

HIPR Top Page, http://www.dai.ed.ac.uk/HIPR/hipr_top.htm, p. 1 (Jan. 10, 2002).

Line Detection, http://www.dai.ed.ac.uk/HIPR2/linedet.htm, pp. 1-8 (Jan. 10, 2002).

Spatial Filters—Gaussian Smoothing, http://www.dai.ed.ac.uk/HIPR2/gsmooth.htm, pp. 1-8 (Jan. 11, 2002).

Glossary—Edge Detectors, http://www.dai.ed.ac.uk/HIPR2/edgdetct.htm, pp. 1-3 (Jan. 10, 2002).

Spatial Filters—Mean Filter, http://www.dai.ed.ac.uk/HIPR2/mean.htm, pp. 1-6 (May 8, 2002).

Feature Detectors—Sobel Edge Detector, http://www.dai.ed.ac.uk/HIPR2/sobel.htm, pp. 1-7 (May 8, 2002)).

Digital Filters, http://www.dai.ed.ac.uk/HIPR2/filtops.htm, pp. 1-3 (May 8, 2002).

Popular Science, What's New, *A Dark and Veiny Night*, p. 10 (Jun. 2001).

* cited by examiner

METHOD AND APPARATUS FOR DETECTING STRUCTURES OF INTEREST

BACKGROUND OF THE INVENTION

1. Field of the Invention

The invention relates to imaging devices, and more particularly to imaging devices for medical and other uses. The invention is particularly useful for imaging vascular structures in patients to aid in the insertion of a needle during venipuncture.

2. Description of the Related Art

Veins and arteries in many patients are difficult to find. This problem is exacerbated in, for example, dehydrated patients, dark-skin patients, and young patients. Further, unskilled technicians have great difficulty in locating subcutaneous structures even in normal patients. Thus, a device to aid in locating such structures is needed.

Attempts at providing such a device include various devices that illuminate skin to enhance location of veins and arteries. These devices use a variety of light sources, such as laser light, infrared light, flashlights, fiber optics, and ultrasonic waves, for illuminating the skin. For example, the device of U.S. Pat. No. 4,817,622 to Pennypacker, et al., which is incorporated herein by reference, illuminates with an infrared light source. Typically, a camera with an image sensor, such as a charged couple device (CCD), or the like is also included to capture an image of the surface below the skin. For example, video and still cameras have been used in such devices. However, none of these devices provided an instrument that produces an image of an acceptably high enough quality to permit rapid and trouble-free finding of vascular structures in patients. In particular, many imaging devices have difficulty handling ambient light, which can interfere with image acquisition and image processing.

In view of the foregoing, it would be desirable to provide a device that permits the detection of a structure or interest, such as, subcutaneous natural or foreign structures in patients and structures above the skin. It would also be desirable to provide a method of using such a device.

SUMMARY OF THE INVENTION

The invention, which is defined by the claims set out at the end of this disclosure, is intended to solve at least some of the problems noted above. A method is provided to detect a structure of interest. Such a target is shaded from ambient light. A first plurality of images including at least three raw images is acquired from the target. Background in the first plurality of images is reduced to minimize or eliminate brightness variation in the images and to generate a first plurality background-reduced images. A second plurality of images including at least two raw images is acquired from the target. Background in the second plurality of images is reduced to generate a second plurality of background-reduced images. Noise in the second plurality of background-reduced images is reduced to generate a noise-reduced image, which is then multiplied to generate an amplified image. A structure of interest is detected in the amplified image.

Also provided is an imaging device including an illuminator to illuminate a target of interest. The illuminator shades the target of interest from ambient light. The imaging device also includes a camera and an image detector, which is operatively connected to the camera. The image detector acquires raw images of the illuminated target of interest and converts the raw images to electrical signals. The electrical signals can be sent to a processor that can be configured to carry out any or all of the steps listed above.

An illuminator, which may be used on an imaging device in a replaceable fashion, is also included. The illuminator includes a lower edge that is configured to be placed on a surface of interest and an upper edge. A middle portion extends from the upper edge to the lower edge and defines an inner area that includes an inner surface to scatter light from the light source.

These, and other, aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings, in which like reference numerals represent like parts throughout and in which.

Figure 1:
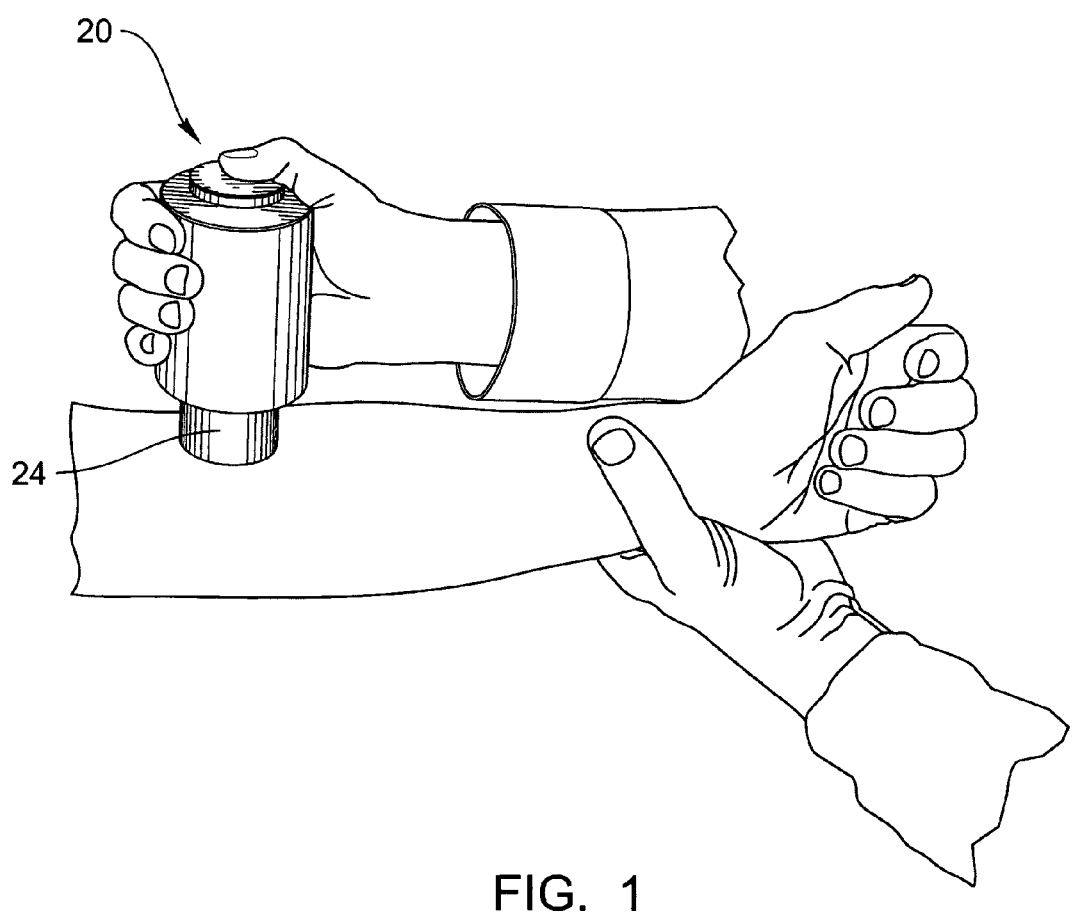
FIG. 1 is an environmental view of an imaging device in accordance with a preferred embodiment of the invention.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

1. System Overview

An imaging device includes a camera, an illuminator to illuminate a target of interest, such as skin, and a display, such as a monitor, for outputting images. In a preferred embodiment, the camera has an image detector 16, such as a charged couple device (CCD). Importantly, the illuminator shades the target of interest from ambient light to prevent background light from entering the target, thereby reducing or eliminating problems associated with ambient light entering the device. Such problems include interference with image acquisition and image processing. Images acquired by the imaging device are pre-processed to reduce background, i.e., brightness variation, reduce noise in the image, and amplify the image. A structure of interest is then detected in the amplified image. In a preferred embodiment, the structure of interest that is detected is a vein. The imaging device and methods described herein can be used to detect structure of interest other than veins. In particular, structures that reflect light differently from their environment can be detected with the imaging device. This makes the invention useful for detecting, e.g., debris in a wound, a hidden object, such as a knife or gun carried on a person.

2. Detailed Description of Preferred Embodiments of the Imaging Device

FIG. 1 shows a preferred embodiment of an imaging device 20 for detecting a target of interest such as a vein in skin of an arm. Now turning to FIG. 2, the imaging device 20 includes a camera 22, an illuminator 24 to illuminate a target of interest, such as skin, and a display 16, such as a monitor, for outputting images. In a preferred embodiment, the display 16 is coupled to the camera 22. The display 16 permits viewing of the surface that is being imaged.

The camera 22 has an image detector (not shown), such as a charged couple device (CCD). It will be understood that other types of image detectors or photo detectors, such as a complimentary metal oxide semiconductor (CMOS), can be used. The CCD has a surface that includes a collection of tiny light-sensitive diodes, which convert photons into electrons. A lens 28 may be used to focus the image on the CCD surface. The diodes of the CCD are oftentimes called photosites and are sensitive to light. The brighter the light that hits a single photosite, the greater the electrical charge that will accumulate at that site. The CCD converts the image to an electrical signal, which is passed through an analog-to-digital converter. The electronic signal, representing pixel values, is sent to a processor together with location information required for pixel (point) location within the image. Pixels representative of brightness can then be stored at a memory and can be manipulated and can be assembled into a processed image by the processor.

Importantly, the illuminator 24 shades the target from ambient light. Shading prevents background light from entering the target to reduce or eliminate problems associated with ambient light entering the device. Such problems include interference with image acquisition and image processing. Representative examples of shaded illuminators are now discussed.

Figure 2:
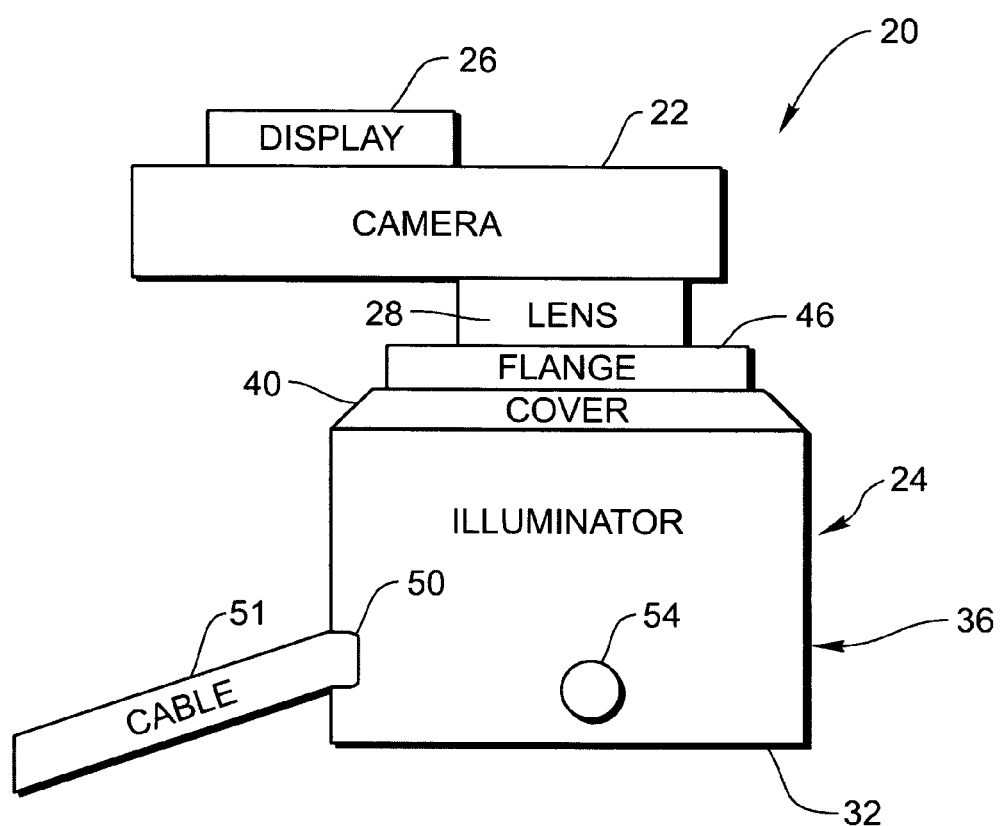
FIG. 2 is a schematic of another preferred embodiment of an imaging device made in accordance with the invention.
Figure 3:
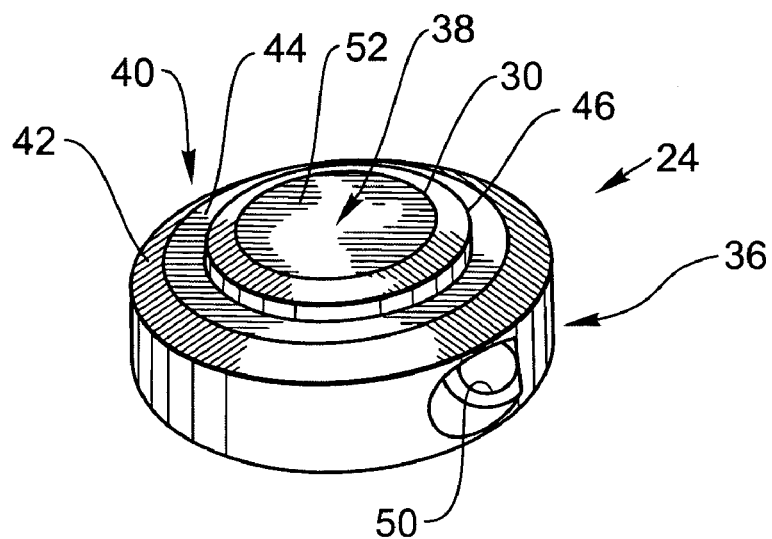
FIG. 3 is a perspective view of an illuminator of the imaging device of FIG. 2.
Figure 4:
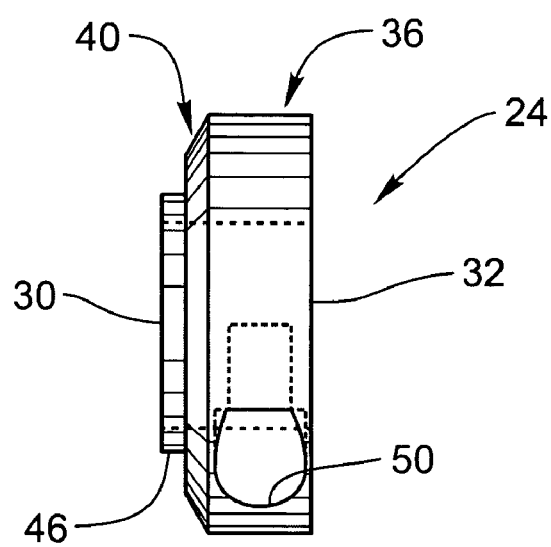
FIG. 4 is a side elevation view of the illuminator of the imaging device of FIG. 3.

In a preferred embodiment, the illuminator 24 has a torus shape, i.e., it is shaped like a doughnut, as illustrated in FIGS. 2–4. The torus-shaped illuminator 24 includes upper and lower edges 30 and 32 and a middle portion 36 that extends from the upper edge 30 to the lower edge 32 to define an inner area 38. The upper edge 30 of the illuminator 24 includes radially extending cover 40, which shades the inner area 38 from ambient light. The cover 40 includes an outer, tapered portion 42 and an inner, non-tapered portion 44, which is parallel to the lower edge 32 of the illuminator 24. An annular flange 46 that extends upwardly from the inner, non-tapered portion 44 and couples the illuminator 24 to the camera 22, preferably via the lens 28, to seal a top of the illuminator 24 from ambient light. The lower edge 32 is applied to a target, for example, the skin of a patient undergoing venipuncture, sealing a bottom of the illuminator 24 from ambient light. Thus, when applied to target, the illuminator 24 is shaded from ambient light.

In the preferred embodiment, torus-shaped illuminator 24, in the middle portion 36 of the illuminator 24 includes a first opening 50, which permits entrance of light from a light source. Preferably the light source is an infrared light source. The light source preferably is in the form of a fiber optic cable 51 (FIG. 2), tubes, or other such sources. In a preferred light source, light of a first wavelength is used to illuminate a target of interest. In another preferred light source, the light source is configured to provide light of a first wavelength, e.g., red light of about 680 nanometers (nm) and a light of a second wavelength, e.g., blue light of about 450 nm. Alternatively, two sources of light are included.

In another preferred embodiment, the first opening is absent, and the light source is preferably located at or near the lower edge 32 of the illuminator 24. In a particularly preferred arrangement, the light source spans from one side of the lower edge 32 to an opposite side of the lower edge 32. For example, columns of light sources are arranged in parallel to span a portion of the inner area 38 defined by the lower edge 32. Another representative example of light arrangement is two sets of parallel columns of light sources arranged at about 90° to each other to provide a grid of light.

The illuminator 24 homogenizes light, such that, regardless of direction, it is relatively uniform. This reduces or eliminates "hot spots," i.e., areas that have more light because of specular reflection, produced by the illuminator 24. Light is reflected and scattered off an inner surface 52 (FIG. 3) of the middle portion 36 of the illuminator 24 to homogenize the light. In a preferred embodiment, scattering is achieved by providing a non-smooth inner surface 52. Light from the inner surface 52 of the illuminator 24 is directed to the target of interest at a plurality of angles.

Figure 5:
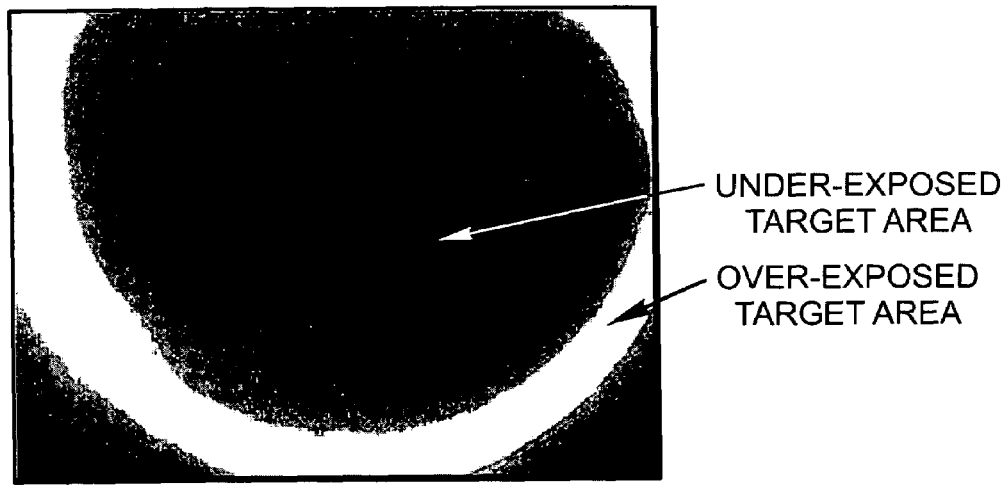
FIG. 5 shows a raw image attained using a preferred embodiment of a method of using the imaging device.

It should be noted that although homogenization of the light reduces or eliminates hot spots produced by the illuminator 24, images produced with the illuminator 24 typically vary in brightness intensity. In general, the brightness variation is characterized in that very bright light exists at or near the illuminator 24 and very dim light exists radially inwardly away from the illuminator 24. This is due primarily to light being able to propagate on a few millimeters before it stops. This is exemplified in FIG. 5, which shows a raw image produced from a torus-shaped illuminator 24. A ring of very bright light exists at the radial outward edge of the raw image, and a circle of dim light exists radially inwardly from the bright ring. This variation of light brightness is preferred to herein as "background light" or "background." Background light is reduced using a preferred embodiment of a method described below.

In a preferred embodiment, the illuminator 24 includes a second opening 54 (FIG. 2) that is configured to permit passage of a needle (not shown) through it. Preferably, the second opening 54 is located in the middle portion 36 of the illuminator 24 near its lower edge 32. As an alternative to the second opening 54, needle entry is achieved by providing, e.g., an opening (not shown) preferably over the upper edge of the illuminator 24. The opening permits a needle to puncture it and, at the same time, is opaque enough so as to shade the target of interest from ambient light.

In a preferred embodiment, the illuminator 24 is a disposable item made of a material, e.g., plastic, such that a new illuminator 24 can be attached to the imaging device after, for example, each patient or when the illuminator 24 becomes worn. Replacing the illuminator 24 after each patient decreases the chances that infectious agents are spread from one patient to the next. Replacing the illuminator 24 when it becomes worn saves money over replacing the entire imaging device 20. It is also possible that the illuminator 24 is fitted with a disposable cover (not shown), which can be replaced to ensure cleanliness.

Figure 6:
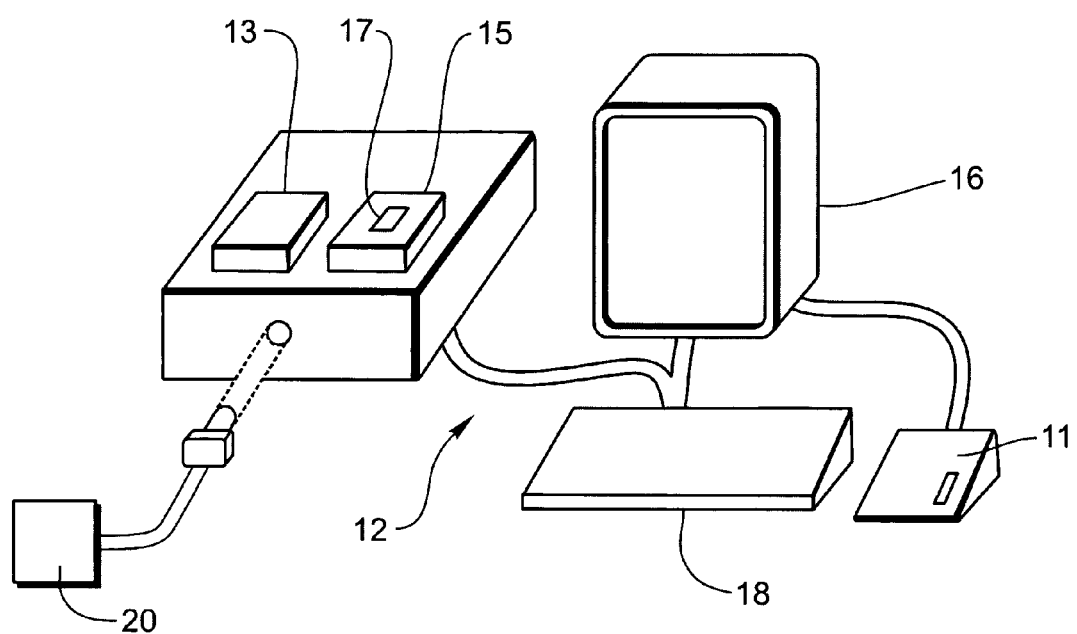
FIG. 6 is a schematic of a computer that can be used to process images obtained with the imaging device.

FIG. 6 shows a computer 12 that can be used to process images acquired with the imaging device 20 (not shown). The computer 12 includes a processor 15 that, in a preferred embodiment, runs software 17 that carries out the preprocessing and detection steps outlined below, a memory 13 that can store raw or processed images, and a monitor 16 for displaying images. In the illustrated computer 12, a keyboard 18 and mouse 11 are also shown. The imaging device 20 (not shown). is coupled to the processor 15, which is processes images and can transfer the processed images to the memory 13. In a preferred embodiment, the processor 15 is a stand-alone processor, such as PC processor, which preferably is a laptop or desktop computer. In another preferred embodiment, the processor 15 is an embedded processor that is built into the imaging device. The standalone processor is coupled to, e.g., the CCD, the memory 13, and the display 16 of the imaging device.

The processor receives input from the CCD after pixels are converted to electrons. The processor carries out the steps outlined below in Section 3, some of which including storing processed images in a memory (not shown). Processed data is transferred to the display 16, which shows the processed image and/or to the memory for further manipulations, which are described in detail below.

3. Use and Operation of the Imaging Device

As best shown in FIG. 1, the illuminator 24 of the imaging device 20 is placed on a target of interest, e.g., skin of a patient undergoing venipuncture. The illuminator 24 shades the target from ambient light. Light from the illuminator 24 is directed towards the surface, e.g., skin. Homogenized light is directed beneath the surface to the subcutaneous tissue containing, e.g., veins. These steps are preferably performed by a high-speed (i.e., 500+ GHz) processor that uses special application software 17.

In a preferred embodiment, at least three raw images are acquired from the target. Each of the images includes image pixels. To facilitate the vein detection process, the image is first subject to some preprocessing by the software 17, which preferably includes the following: (a) background reduction to decrease brightness variation in the image, (b) noise reduction to decrease random variation in the image, and (c) amplification to increase the strength of the image.

a. Background Reduction

Figure 7:
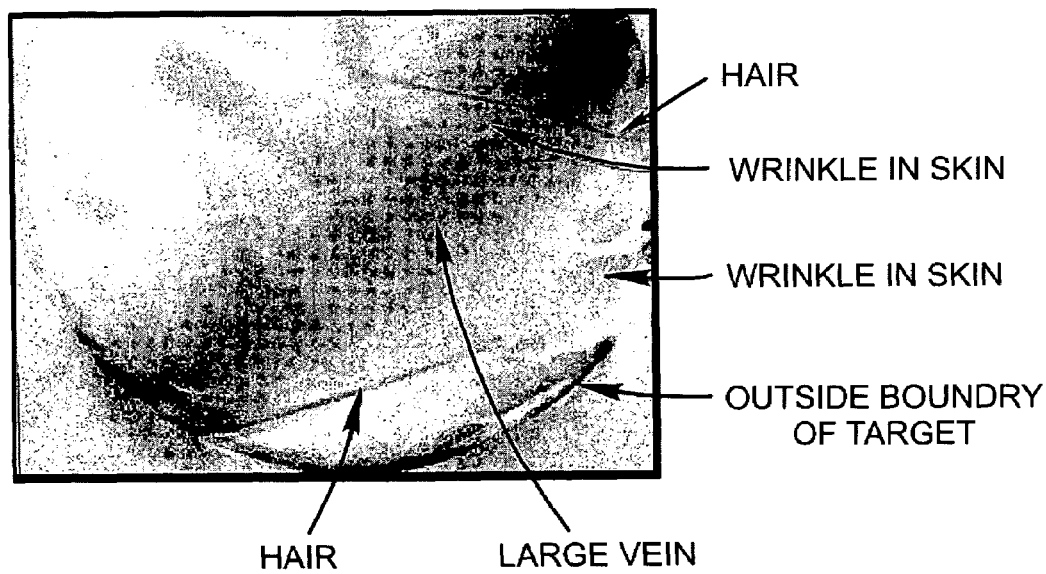
FIG. 7 illustrates an image after a preferred embodiment of a background reduction step has been performed on a raw image.

Background reduction minimizes or eliminates brightness variation in the image, which, in general, is characterized in that very bright light exists at or near the illuminator 24 and very dim light exists radially inwardly from the illuminator described in detail above in Section 2. Background reduction increases the uniformity in the brightness of the light. An exemplary image after background reduction is shown in FIG. 7. In comparison to the raw image shown in FIG. 5, brightness variation in the image of FIG. 7 is greatly minimized.

A background-reduced image can be generated from images acquired at different locations along a target or at the same location on a target. A benefit of acquiring images from different locations is that formations, such as hairs, will not interfere with the acquisition of the image.

In a first preferred embodiment of background reduction, the three raw images are median filtered. It should be noted that at least three images are necessary to determine a median of the images. However, more images can be median filtered. For simplicity sake, the following will discuss processing three images. At each pixel location, median filtering considers each pixel in the three images and computes a median value for pixels at each pixel location. From the middle (or median) pixel values for each pixel location, a background-reduced image is generated. The background-reduced image can be stored in the memory for further processing as discussed below. The pixels of the stored images can be stored in an array or can be concatenated. In a preferred embodiment, the background-reduced image is stored in the memory in an array, which is referred to as a median array. For example, the median array can be updated to add newly acquired images, the median array can be subtracted off subsequent images, and multiple median arrays can be used to generate a mean array. These are detailed below.

In a second preferred embodiment of the background reduction, a fit surface is applied to the background to form a background-reduced image. In a preferred embodiment, a polynomial, two-dimensional surface is determined that describes typical background brightness variation. The polynomial, two-dimension surface is then fit to the background. An exemplary polynomial for this is N(counts in x,y)=$A+Bx+Cx^2+Dx^3+Ey+Fy^2+Gy^3$. In contrast to median filtering, which typically is calculated each time that a new structure of interest is being detected, the same predetermined polynomial can be applied each time. Thus, this preferred embodiment of background reduction takes less time than the median filtering, because median filtering is normally performed repeatedly. It should be noted that with median filtering, it may be possible to determine the background-reduced image once and to reuse or reapply it multiple times.

In a third preferred embodiment of the background reduction, a spline fit is applied to the background to form a background-reduced image. In this preferred embodiment, typical background brightness variation is represented by a curve known as a spline. A "spline curve" is a shape created when a user specifies a series of points and the computer software draws a curve that smoothly approaches these points. Splines may be described mathematically as polynomial functions, which provide smooth curves with continuous first and second order derivatives. This preferred embodiment also has the advantage of not having to recalculate the background image each time that a new structure of interest is being detected. Instead, the predetermined spline fit can be applied each time.

Where the background-reduced image is generated by median filtering, the processor calls up the background-reduced image from the memory. In a pixel-by-pixel fashion, the background-reduced image is subtracted from a subsequent image or images to generate the background-subtracted image.

Where the background-reduced image is generated by applying a fit surface to the background, brightness variance reduction is achieved by subtracting the polynomial from a subsequent image or images to generate a background-subtracted image.

Where the background-reduced image is generated by applying a spline fit to the background, brightness variance is reduced by subtracting the spline fit from a subsequent image or images to reduce the background in the subsequent image and to generate a background-subtracted image.

b. Noise Reduction

Figure 8:
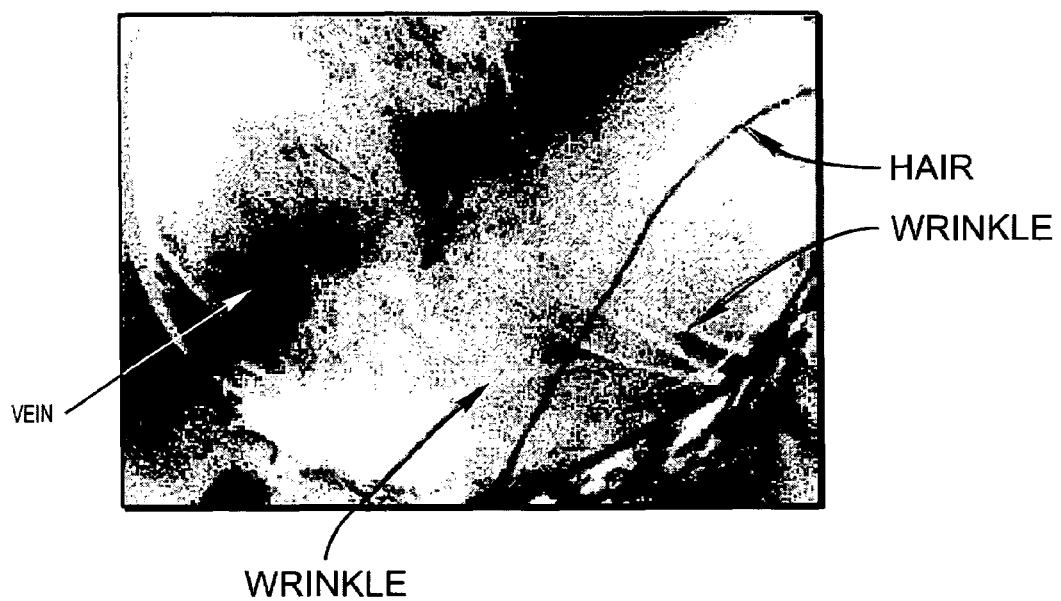
FIG. 8 shows an image after a preferred embodiment of a noise reduction step has been performed on a background-reduced image.

Noise, i.e., aberrant pixel signals, may be caused a wide range of sources, e.g., variations in the detector sensitivity, environmental variations, the discrete nature of radiation, and transmission or quantization errors. Reducing noise in images generates a noise-reduced image that has less intensity variation between different pixels. An exemplary noise-reduced image is shown in FIG. 8. The appearance of the dark vein is enhanced when compared to that in FIG. 7.

Noise-reduced image is preferably generated from images acquired at the same location on a target. However, the noise-reduced image can also be generated from images acquired at different locations.

Preferably, noise is reduced by mean filtering. In a preferred embodiment, mean filtering is performed by the processor on multiple background-substrated images. At each pixel location, pixels from multiple images are added together in a pixel-by-pixel fashion and then divided by the number of images to create a mean pixel value for each pixel location. After mean filtering, pixels collectively form a noise-reduced image.

Pixels representing a structure of interest are coherent and, thus, add coherently. By "coherent" it is meant there is a fair amount of congruity or consistency between one pixel and a neighboring pixel. In contrast, noise in the pixels is incoherent and adds incoherently. The coherency of the structure of interest increases the contrast of the noise-reduced image when images are added together. On the other hand, incoherent noise in the pixels incoherently adds to the mean to reduce the noise in the mean image. The signal-to-noise ratio increases approximately as the square root of the number of images are added together.

c. Amplification of Image

The noise-reduced image is amplified with a predetermined gain to generate an amplified image. Preferably, a gain of at least 10, and more preferably, a gain in the range of 100 to 2000, or even more is applied to increase the strength of the noise-reduced image to create an amplified image.

At the conclusion of pre-processing steps, the amplified image now has a more uniform background with the brightness variations reduced. Additionally, noise in the amplified image has been reduced. Furthermore, contrast has been amplified. With these pre-processing steps performed, detection of a structure of interest is more easily accomplished.

d. Detection of a Structure of Interest

A structure of interest is detected in the amplified image. Detecting can be accomplished through a variety of methods, primarily depending on a characteristic of the structure of interest. Representative examples of methods to detect a structure of interest include using line detection and/or using edge detection, and applying a matched filter for a structure of interest to the amplified image.

If, for example, the structure of interest has at least some linear components, such as a vein, shrapnel, or a knife, line detection can be used to detect the structure. In a preferred embodiment of line detection, the amplified image is processed through a line detector. Preferably, this is accomplished with a convolution technique that uses a convolution kernel tuned to detect the presence of a line.

For non-linear structures, edge detection can be used. In a preferred embodiment of edge detection, the image pixels are processed through an edge detector. Preferably, this is accomplished in the spatial domain by convolving the image with an appropriate kernel, which is tuned to detect the presence of an edge, in the spatial domain. Alternatively, the edge detection is achieved by applying a high-pass frequency filter in the Fourier domain.

Additionally, a matched filter can be used to detect a structure of interest where size and orientation of the structure is known in advance. For example, to detect a vein, a matched filter to detect, e.g., a curved line representative of a vein, can be used. Additionally, a branched structure representative of a branch in a vein or other known substructures of a vein can be used to detect a vein.

e. Multiple Detections at Different Wavelengths to Diminish or Eliminate at Least Some Undesired Objects Certain features, such as hairs, have the same reflectivities of light regardless of the light's color. In contrast, other features, such as veins and arteries, reflect differently colored light differently. For example, hair reflects blue light and red light in a similar manner. Veins, in contrast, differentially reflect, e.g., blue and red light. This difference permits the use of the illuminator 24 at a first wavelength and then at a second wavelength through the pre-processing steps to generate an amplified image of a first wavelength (a first wavelength image) and of a second wavelength (a second wavelength image). One of the first and second wavelength images is subtracted from the other. This subtraction of undesired structures generates an image having the vein present without interference from, e.g., the hairs. With undesired structures removed, the structure of interest is detected. The removal of undesired structures dramatically increases the ability to find a vein.

f. Estimating the Width and Depth of a Structure of Interest

The imaging device 20 is used to estimate the width and depth of a vein. Two factors are used for this estimation. First, hemoglobin in veins absorbs light, leading to reduced light respectively. Larger veins contain more hemoglobin than smaller veins. Therefore, larger veins reflect less light than smaller veins. Second, deeper veins scatter light more than shallow, or near surface veins. These two factors are used to estimate in the following method to determine the width and depth of a vein.

The preferred embodiment described immediately below, plots data on a graph. It should be noted that plotting of data is not necessary. For example, data can be manipulated by the processor to make the determinations described below.

Attention is now directed to FIGS. 9A through 9D. In a preferred embodiment, light reflectivity is plotted on y-axis and a horizontal position across an image is plotted on an x-axis. A baseline B of light reflectivity is determined. A light reflectivity difference is determined based on a difference between baseline B and the depressed measurement of light reflectivity on the y-axis. This difference is termed height H. On the y-axis, the length of the horizontal position across the image for which there is the depressed measurement of light reflectivity is calculated as a width W. A width to height (W:H) ratio is also determined.

Figure 9A:
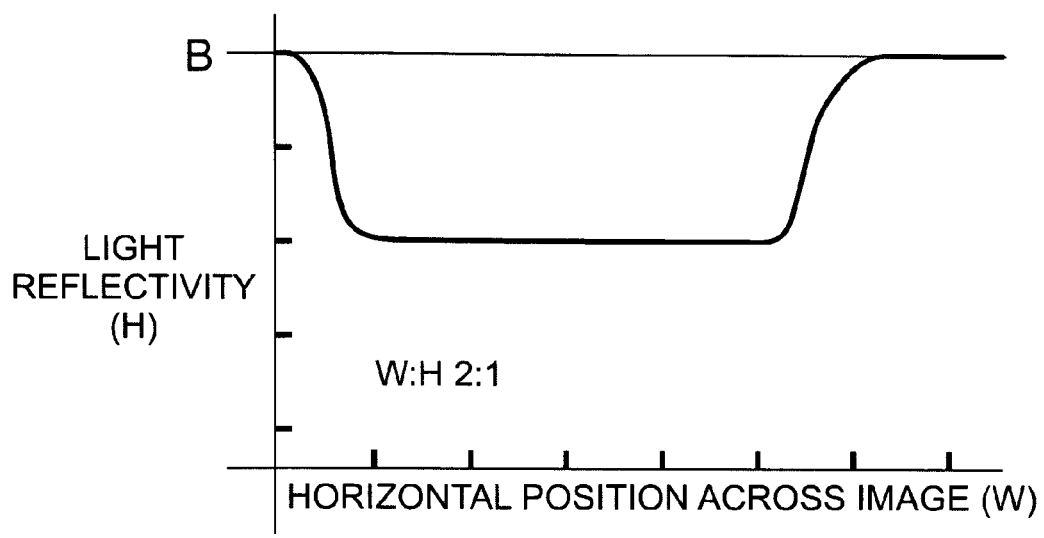
FIGS. 9A to 9D are graphs plotting light intensity on the y-axis and horizontal position across an image on the x-axis, showing a preferred embodiment of a method of determining depth and width of a vein.

For the data represented in FIG. 9A, the W is about 4 and the H (light reflectivity difference) is about 2, giving a width to height (W:H) ratio of about 2:1. The W, H, and W:H ratio indicated that the vein is large (the height is large due to the vein absorbing a lot of light) and the vein is shallow (the width and height measurements are close 2:1, indicating that the width has not been widened due to lack of scattering).

Figure 9B:
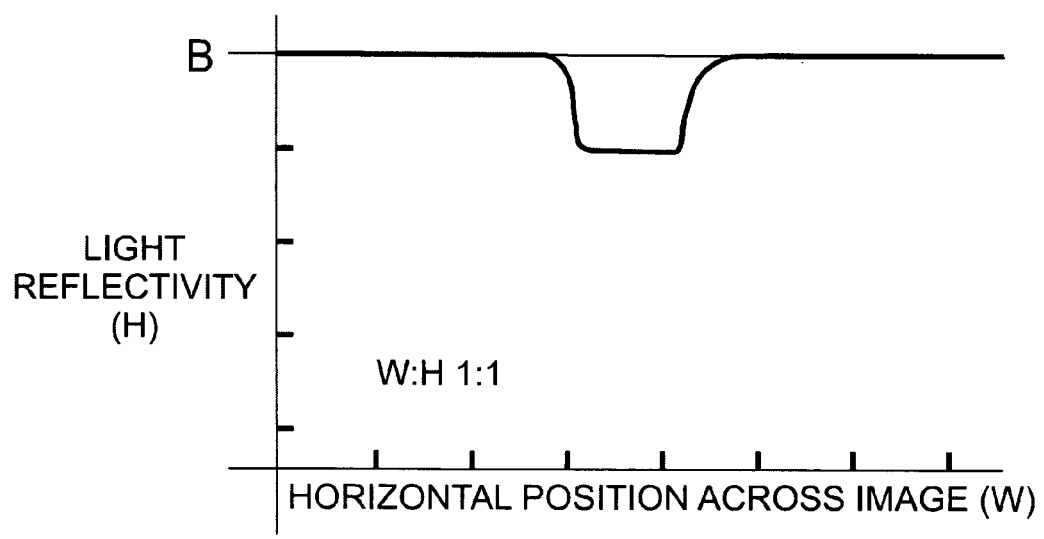

For the data of FIG. 9B, the W is about 1 and the H is about 1, generating a W:H ratio of about 1:1. The W, H, and W:H ratio indicated that the vein is small (the height is relatively small due to the vein not absorbing a lot of light)

and the vein is shallow (the width and height measurements are close, the width has not been widened due to lack of scattering).

Figure 9C:
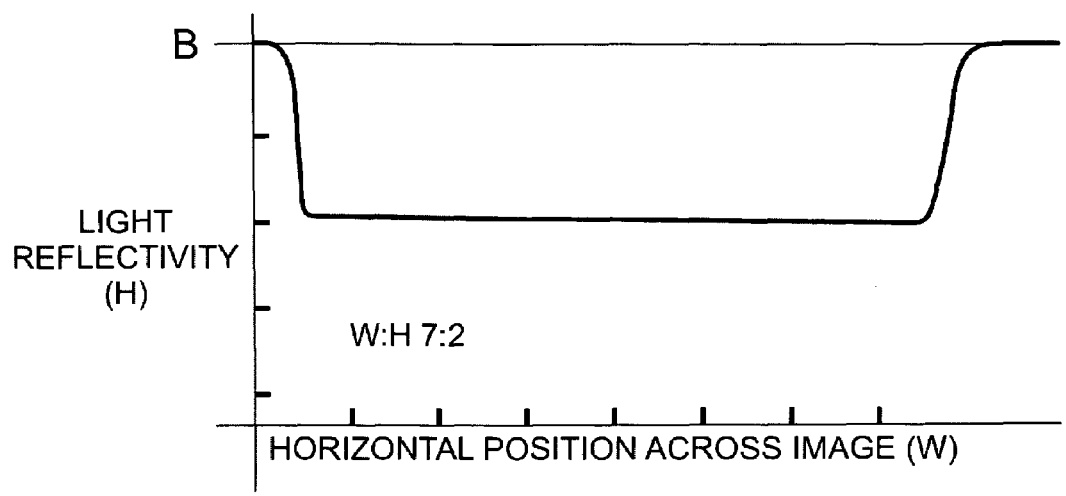

For the data represented in FIG. 9C, the W is about 7 and the H is about 2, giving a width to height (W:H) ratio of about 7:2. The W, H, and W:H ratio indicated that the vein is large (the height is larger due to the vein absorbing a lot of light) and the vein is deep (the width is much larger than the height due to scattering of light).

Figure 9D:
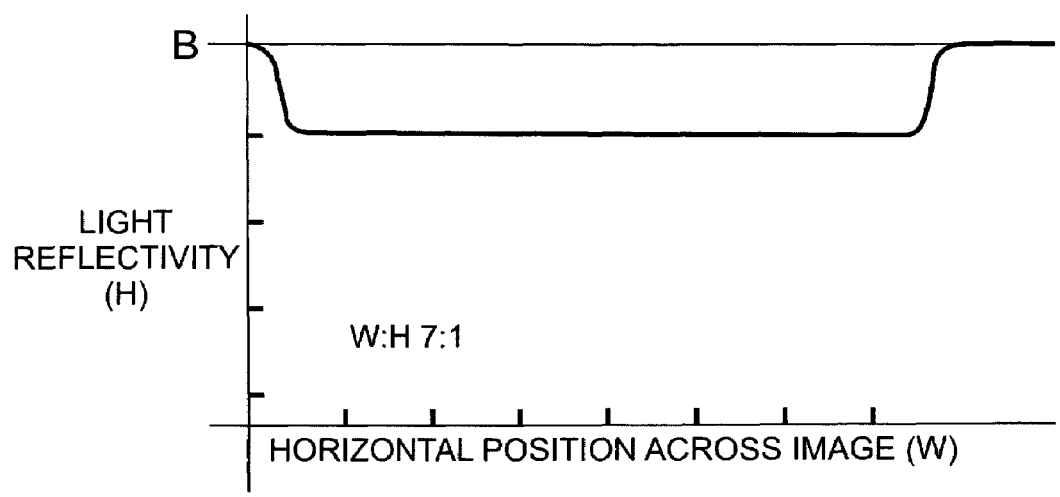

For the data represented in FIG. 9D, the W is about 7 and the H is about 1, giving a width to height (W:H) ratio of about 7:1. These measurements indicated that the vein is small (the height is relatively small due to the vein not absorbing a lot of light). The 7:1 W:H ratio indicates that the vein is deep.

Thus, it can be seen that by examining the width, height, and width to height ratios of the reflectivity data and the horizontal position across the images, the imaging device 20 can be used to estimate the width and depth of a vein, which can dramatically improve the phlebotomist's ability to find a vein.

It is understood that the various preferred embodiments are shown and described above to illustrate different possible features of the invention and the varying ways in which these features may be combined. For example, while one preferred embodiment is used to detect veins in skin, other embodiments may be used to detect other objects such as slivers, shrapnel, or dirt in skin or concealed objects likes knives hidden in clothing. Further, while the illuminator is described as torus-shaped herein, other shapes are possible.

Apart from combining the different features of the above embodiments in varying ways, other modifications are also considered to be within the scope of the invention. The invention is not intended to be limited to the preferred embodiments described above, but rather is intended to be limited only by the claims set out below. Thus, the invention encompasses all alternate embodiments that fall literally or equivalently within the scope of these claims.

What is claimed is:

1. A method of detecting a structure comprising the steps of:
   (A) providing a cylindrical illuminator having a light source;
   (B) shading a target from ambient light with a portion of the illuminator;
   (C) illuminating the target with the light source;
   (D) acquiring from the target a plurality of images;
   (E) reducing background in the plurality of images to generate a second plurality of background-reduced images;
   (F) reducing noise in the plurality of background-reduced images to generate a noise-reduced image;
   (G) applying the noise-reduced image a predetermined gains of at least 10 to generate an amplified image;
   (H) performing steps (A) through (G) with a first wavelength of light to generate a noise-reduced image at a first wavelength to generate an amplified image of the first wavelength; and further comprising repeating steps (A) through (G) with a second wavelength of light to generate an amplified image at the second wavelength that includes noise-subtracted pixels at the second wavelength; and subtracting the amplified image at the first wavelength from the amplified image at the second wavelength to generate a color-subtracted image; and
   (I) detecting a structure of interest in the color-subtracted image.

2. A method of claim 1, wherein the reducing background as provided for in step (E) comprises filtering the plurality of images with a median filter to generate the background-reduced images.

3. A method of claim 1, where in the reducing background as provided for in step (E) comprising applying a fit surface to the background to form the background-reduced image.

4. A method of claim 3, wherein the applying the fit surface step comprises fitting the background to a polynomial, two dimensional surface.

5. A method of claim 4 wherein the polynomial comprises $N(\text{counts in x,y})=A+Bx+Cx^2+Dx^3+Ey+Fy^2+Gy^3$.

6. A method of claim 1, wherein the reducing noise as provided for in step (F) comprises generating a mean image of the plurality of images to generate the noise-reduced image.

7. A method of claim 6, wherein the reducing noise step comprises adding raw images of the plurality of images together, and dividing the added images by the number of images to generate the noise-reduced image.

8. A method of claim 1, furthering comprising store plurality of background-reduced images and the noise-reduced image.

9. A method of claim 1, further comprising acquiring from the target a subsequent image.

10. A method of claim 1, wherein the acquiring step as provided for in step (D) comprises:
    (a) homogenizing the light from the light source; and
    (b) applying the homogenized light to the surface of interest.

11. A method of claim 1, wherein the detecting step as provided for in step (I) comprises processing the color-subtracted image through a line detector.

12. A method of claim 1, wherein the detecting step as provided for in step (I) comprises processing the noise-reduced image pixels through an edge detector.

13. A method of claim 1, wherein the detecting step as provided for in step (I) comprises applying a matched filter for a structure of interest to the color-subtracted image.

* * * * *